United States Patent
Taneja

(10) Patent No.: US 8,653,128 B1
(45) Date of Patent: Feb. 18, 2014

(54) VETERINARY COMPOSITION AND METHOD

(76) Inventor: Jugal K. Taneja, Tampa, FL (US)

( * ) Notice: Subject to any disclaimer, the term of this patent is extended or adjusted under 35 U.S.C. 154(b) by 0 days.

(21) Appl. No.: 13/427,966

(22) Filed: Mar. 23, 2012

(51) Int. Cl.
*A01N 43/56* (2006.01)

(52) U.S. Cl.
USPC ............................................. 514/407

(58) Field of Classification Search
USPC ............................................. 514/407
See application file for complete search history.

(56) References Cited

FOREIGN PATENT DOCUMENTS

| | | | |
|---|---|---|---|
| CN | 101804048 | * | 8/2010 |
| WO | WO 2010026370 | * | 3/2010 |

OTHER PUBLICATIONS

Glossary of medical education terms, Institute of International Medical Education. http://www.iime.org/glossary.htm Accessed in Mar. 2013.*

Rust MK. Innovations and Future Directions in the Control of Cat Fleas on Cats and Dogs. Proceedings 8th International Symposium on Ectoparasites of Pets (ISEP), pp. 35-40, 2005.*

* cited by examiner

*Primary Examiner* — Wu-Cheng Winston Shen
*Assistant Examiner* — Yih-Horng Shiao

(57) ABSTRACT

A stable liquid pharmaceutical formulation containing an N-phenylpyrazole derivative, a crystallization inhibitor/viscolizer and a solvent/co-solvent system comprised of a glycol ether solvent and at least one mono alkyl ester co-solvent; and the use of such a formulation for the prevention and/or treatment of infestations with fleas and ticks.

1 Claim, No Drawings

VETERINARY COMPOSITION AND METHOD

BACKGROUND OF THE INVENTION

1. Field of the Invention

The present invention relates to a veterinary composition and method and more particularly pertains to veterinary compositions and methods of use for preventing and treating fleas and ticks.

2. Description of the Prior Art

The use of veterinary techniques is known in the prior art. More specifically, veterinary techniques previously devised and utilized for the purpose of preventing and treating fleas and ticks are known to consist basically of familiar, expected, and obvious structural configurations, notwithstanding the myriad of designs encompassed by the crowded prior art which has been developed for the fulfillment of countless objectives and requirements.

The control of fleas and other external parasites of domestic animals has become an important part of domestic life. The substantial increase in pet ownership has meant that the market for such products has increased dramatically.

To undertake control of such parasites pet owners have a variety of options:
  Bathing the pet in a medicated wash
  Spraying the pet with a medicated solution
  Placing a pesticide-impregnated collar around the neck of the pet
  Giving the pet a tablet containing an effective ectoparasiticide compound able to reach an efficacious level in the blood More recently it has become popular to treat pets for fleas and ticks by applying a medicated liquid formulation to one or more spots on the back of the pet. To achieve this all-over efficacy such formulations rely either on the transdermal absorption, or topical translocation of the ectoparasiticide to other parts of the body. A number of different ectoparasiticides have proven to be effective when delivered in this manner. Of particular note is the phenylpyrazole derivative (5-amino-1-[2,6-dichloro-4-(trifluoromethyl)phenyl]-4-(trifluoromethylsulfinyl)-1H-pyrazole-3-carbonitrile), fipronil, marketed under the trade name FRONTLINE Spot-On.

Patent applications EPO 295 117 and EP 0 352 944 describe fipronil, as well as, a large family of N-phenylpyrazoles, which have a very broad spectrum of activity, including antiparasitic activities.

Although they are effective when delivered in the manner described above, N-phenylpyrazole derivatives are sometimes difficult to formulate since they are not readily soluble in the common excipients used for topical pesticide treatments. Moreover, when formulated in such excipients, the formulations can have a significant potential for crystallisation.

To address this issue, there has been a number of alternative formulation systems proposed that combine a crystallisation inhibitor with one or more solvent/co-solvents. For example;

U.S. Pat. No. 6,395,765 (Merial) addresses the problem of crystallisation of the N-phenylpyrazole active through the use of a combination of a crystallization inhibitor; an organic solvent having a dielectric constant of between 10 and 35, preferably of between 20 and 30; an organic co-solvent having a boiling point below 100° C., preferably below 80° C., and a dielectric constant of between 10 and 40, preferably of between 20 and 30. In the formulation marketed under this patent (FRONTLINE/FRONTLINE Plus) the crystallisation inhibitor used is polyvinylpyrrolidone combined with a surfactant; the solvent used is Diethylene glycol monoethyl ether solvent; and the co-solvent is ethanol.

Other more recent patent examples include:

WO 2010092355 (Cipla) which proposes use of a crystallisation inhibitor such as Polyvinyl pyrollidone in conjunction with a solvent system selected from polyoxyethylenated ester of sorbitan, a polyoxyethylene castor oil derivative, propylene glycol; a fatty acid ester of propylene glycol such as propylene glycol monocaprylate, propylene glycol monolaurate; an oleoyl macrogol glyceride; a caprylocaproyl macrogol glyceride; a polyethylene glycol; a copolymer of ethylene oxide & propylene oxide; or a combination thereof. Furthermore, this patent has flash point constraints along with constraints on the use of a surfactant.

US 20110060023 (Donnelly) proposes the use of at least one crystallisation inhibitor such as polyethylene glycol or polyethylene glycol hydrogenated castor oil combined with a solvent system made up of up to 8% of one C1-C6 alcohol co-solvent combined with at least one organic solvent which is not the C1-C6 alcohol co-solvent. The crystallization inhibitor is present in from 2% to 20% by weight of the formulation.

CN 101804048 (Shanghai Hanwei Biopharmaceutical) proposes the use of a crystallisation inhibitor selected from dimethylsulfoxide, cellulose acetate butyrate, N-methylpyrrolidone, N,N-dimethylacetamide, glycerol acetone, isosorbide dimethyl ether and propylene carbonate, combined with at least one solvent and at least one co-solvent. The preferred formulation also suggests the inclusion of DMSO as a co-solvent.

GB 2464449 (Norbrook) suggests use of a glycol ether combined with butanol and/or DMSO.

Many of these recent patents lack exact detail on the purpose of each specific excipient and also do not provide examples of how a formulation could be prepared using each of the excipient combinations claimed and appear to be lacking the necessary enablement.

In this respect, the veterinary compositions and methods according to the present invention substantially departs from the conventional concepts and designs of the prior art, and in doing so provides an apparatus primarily developed for the purpose of preventing and treating fleas and ticks.

Therefore, it can be appreciated that there exists a continuing need for a new and improved veterinary compositions and methods which can be used for preventing and treating fleas and ticks. In this regard, the present invention substantially fulfills this need.

SUMMARY OF THE INVENTION

In view of the foregoing disadvantages inherent in the known types of veterinary techniques now present in the prior art, the present invention provides an improved veterinary compositions and methods. As such, the general purpose of the present invention, which will be described subsequently in greater detail, is to provide a new and improved veterinary compositions and methods and method which has all the advantages of the prior art and none of the disadvantages.

To attain this, the present invention essentially comprises a stable liquid pharmaceutical formulation containing an N-phenylpyrazole derivative, a crystallisation inhibitor/viscolizer and a solvent/co-solvent system comprised of a glycol ether solvent and at least one mono alkyl ester co-solvent; and the use of such a formulation for the prevention and/or treatment of infestations with fleas and ticks.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved veterinary compositions and methods which has all of the advantages of the prior art veterinary techniques and none of the disadvantages.

It is another object of the present invention to provide a new and improved veterinary compositions and methods which may be easily and efficiently manufactured and marketed.

An even further object of the present invention is to provide a new and improved veterinary compositions and methods which is susceptible of a low cost, and which accordingly is then susceptible of low prices of sale to the consuming public, thereby making such veterinary compositions and methods economically available to the buying public.

Even still another object of the present invention is to provide a veterinary compositions and methods for preventing and treating fleas and ticks.

Lastly, it is an object of the present invention to provide new and improved veterinary compositions and methods of use for preventing and treating fleas and ticks.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

DESCRIPTION OF THE PREFERRED EMBODIMENT

In order to provide an alternative N-phenylpyrazole formulation, the inventor has developed a formulation which is simple to prepare, addresses the crystallisation problem, and uses commonly acceptable excipient materials.

Thus, the subject of the present invention is a stable liquid pharmaceutical formulation, characterized in that it contains: 5-amino-1-[2,6-dichloro-4-(trifluoromethyl)phenyl]-4-(trifluoromethylsulfinyl)-1H-pyrazole-3-carbonitrile (fipronil) as an active ingredient, a glycol ether as the main carrier, a crystallisation inhibitor/viscolizer, and mono alkyl ester co-solvent or co-solvents.

In the preferred form, the mono alkyl ester co-solvent(s) used is ethyl acetate and optionally ethyl lactate.

Ethyl acetate is the ester of ethanol and acetic acid. It has a boiling point of 77.1° C. and a dielectric constant of 6.

Ethyl lactate, also known as lactic acid ethyl ester, is a monobasic ester formed from lactic acid and ethanol. It has a boiling point of 155° C. and a dielectric constant of approximately 13.1

According to the invention, the liquid pharmaceutical formulation is, in particular, intended to be administered topically to cats or dogs.

Within the liquid pharmaceutical formulation used in accordance with the invention, fipronil preferably represents from 10 to 200 g approximately per liter of formulation, and even more preferably, from 50 to 150 g approximately per liter.

The pharmaceutical formulation used in accordance with the invention may also contain one or more other excipients that can, for example, be chosen from thickeners, dyes, fragrances and antioxidants, among which mention may, by way of non-limiting example, be made of butylhydroxyanisol, butylhydroxytoluene, propyl gallate, ascorbyl palmitate, and mixtures thereof.

When one or more antioxidants are present, the antioxidants preferably represent from 0.005% to 2% by weight approximately and even more preferably from 0.01% to 0.1% by weight approximately, relative to the total volume of the formulation.

In addition to fipronil, the pharmaceutical formulation may also comprise one or more additional antiparasitic active ingredients. By way of additional antiparasitic active ingredient, mention may particularly be made of acaricides, such as amitraz or cymiazole, insect growth regulators, often referred to as IGRs, for fleas and ticks, such as pyriproxyfen and s-methoprene, endoparasiticides such as avermectins and derivatives thereof, for instance ivermectin, abamectin, doramectin, eprinomectin, moxidectin, selamectin, milbemycins, and also compounds that are active against sandflies and ectoparasites of domestic animals.

After it has been prepared, the pharmaceutical formulation is preferably packaged in single-dose pipettes.

Another subject of the present application is the use of a liquid pharmaceutical formulation as described above, for the prevention (protection) and/or treatment of infestations with fleas in domestic animals, and in particular, in dogs or cats.

According to this use, said formulation is intended to be applied by direct application to the skin of the animal, at the level of the shoulder blades, or on a dorsal line starting from the base of the tail, and going up to the neck.

The amount of the formulation to be administered can range from 0.3 to 1.5 ml approximately, preferably 0.5 ml approximately, in cats and from 0.3 to 6.0 ml approximately in dogs, depending on the weight of the animal under consideration and on the dosage.

The volume to be applied according to the invention should preferably correspond to a unit dose of fipronil ranging from 0.3 to 60 mg per kg of body weight, and even more preferably from 5 to 15 mg per kg of body weight.

Thus, according to a preferred embodiment of the invention, said formulation is intended to be administered at a unit dose of fipronil ranging from 0.3 to 60 mg per kg of body weight, and even more preferably from 5 to 15 mg per kg of body weight.

Preferred Method of Preparation

The preferred formulations of the invention are set out in the following tables:

| % w/v | Formulation 1 | Formulation 2 | Formulation 3 |
|---|---|---|---|
| Fipronil | 10% | 10% | 10% |
| BHA | 0.02% | 0.02% | 0.02% |
| BHT | 0.01% | 0.01% | 0.01% |
| Ethyl Lactate | 10% | — | 5.0% |
| Ethyl Acetate | — | 10% | 5.0% |
| CAB—Cellulose Acetate Butyrate (0.1) | 2% | 2% | 2% |
| Diethylene Glycol Monoethyl Ether | To vol | To vol | To vol |

| % w/v | Formulation 4 | Formulation 5 | Formulation 6 |
|---|---|---|---|
| Fipronil | 10% | 10% | 10% |
| BHA | 0.02% | 0.02% | 0.02% |
| BHT | 0.01% | 0.01% | 0.01% |
| Ethyl Lactate | 10% | — | 5.0% |
| Ethyl Acetate | — | 10% | 5.0% |
| Polyvinylpyrollidone | 5% | 5% | 5% |
| Polysorbate 80 | 5% | 5% | 5% |
| Diethylene Glycol Monoethyl Ether | To vol | To vol | To vol |

The function of the various ingredients is as follows:

| Function | Material |
|---|---|
| Active | Fipronil |
| Crystallization inhibitor/Viscolizer | Polyvinylpyrollidone and/or Cellulose Acetate Butyrate |
| Organic solvent | Diethylene glycol monoethyl ether |
| Co-organic solvent/s | Ethyl Acetate and/or Ethyl Lactate |
| Antioxidant | BHT |
|  | BHA |

Method of Preparation
1. Mix Ethyl Acetate, optionally Ethyl lactate, and Diethylene Glycol Monoethyl Ether
2. Add Butylated Hydroxyanisole and Butylated hydroxytoluene and mix until dissolved
3. Add Fipronil, mix until dissolved;
4. Add Cellulose Acetate Butyrate or Polyvinylpyrollidone and optionally a surfactant; mix until completely dissolved
5. Complete the volume with Diethylene Glycol Monoethyl Ether and mix
6. Send sample for QC Stability The formulations of the preferred invention were subject to accelerated stress testing and compared to the currently marketed FRONTLINE Spot-On (Merial) formulation. The result of testing at 60° C. for 3 weeks is as follows:

| % w/v | FRONTLINE SPOT-ON | Formulation 1 | Formulation 2 | Formulation 3 |
|---|---|---|---|---|
| Fipronil | 10% | 10% | 10% | 10% |
| Appearance (4) | Pale yellow | Colorless | Colorless | Colorless |
| Appearance (60) | Light yellow | Light yellow | Pale yellow | Light yellow |
| Viscosity (60, mPa · s) | 12.42 | 11.35 | 11.34 | 11.22 |
| Fipronil % * | 100.1% | 98.9% | 99.3% | 99.8% |

| % w/v | Formulation 4 | Formulation 5 | Formulation 6 |
|---|---|---|---|
| Fipronil | 10% | 10% | 10% |
| Appearance (4) | Colorless | Colorless | Colorless |
| Appearance (60) | Light yellow | Pale yellow | Pale yellow |
| Viscosity (60, mPa · s) | 11.21 | 11.62 | 11.79 |
| Fipronil % * | 99.5% | 98.3% | 100.2% |

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A dimethyl sulfoxide free (DMSO-free) topical antiparasitic composition for a domestic animal comprises:
   a) an antiparasitic active ingredient that is fipronil, and at least one additional antiparasitic active ingredient selected from the group consisting of acaricides, amitraz, cymiazole, insect growth regulators, pyriproxyfen, s-methoprene, avermectins, ivermectin, abamectin, eprinomectin, moxidectin, selamectin, and milbemycin;
   b) a glycol ether main solvent that is selected from the group consisting of diethylene glycol monoethyl ether, diethylene glycol monomethyl ether, diethylene glycol monobutyl ether, dipropylene glycol monoethyl ether, dipropylene glycol monomethyl ether, ethylene glycol monoethyl ether, ethylene glycol monomethyl ether, propylene glycol monoethyl ether, propylene glycol monomethyl ether, propylene glycol, PEG, and combinations thereof;
   c) a mono alkyl ester co-solvent having a dielectric constant of less than 10 or greater than 40 and/or a boiling point greater than 100° C., and the co-solvent comprising ethyl acetate and ethyl lactate;
   d) a crystallization inhibitor that is Solketal and at least one additional crystallization inhibitor/viscolizer selected from the group consisting of cellulose acetate butyrate, N-methylpyrrolidone, N,N-dimethylacetamide, Polyvinylpyrrolidone, isosorbide dimethyl ether, and propylene carbonate; and e) an antioxidant that is ascorbyl palmitate and at least one additional antioxidant selected from the group consisting of butylated hydroxytoluene (BHT), butylated hydroxyanisole (BHA), and propyl gallate, and characterized in that the antioxidant has a percent weight per volume (% w/v) of total composition of from about 0.005% to about 2%;

said composition further characterized in that the percentages of weight per volume (% w/v) of components present in the composition are as follows: total antiparasitic active ingredient from about 1% to about 20%; total crystallization inhibitor from about 1% to about 20%; total co-solvent from about 1% to about 15%; and at least one excipient and total main solvent, complement to 100%.

* * * * *